United States Patent
Lang et al.

[11] Patent Number: 5,830,413
[45] Date of Patent: Nov. 3, 1998

[54] DEVICE FOR PROCESSING SLIDE-MOUNTED SAMPLES

[75] Inventors: Alfred Lang, Oberhausen; Horst Menzler, Bernried, both of Germany

[73] Assignee: Boehringer Mannheim GmbH, Mannheim, Germany

[21] Appl. No.: 606,991

[22] Filed: Feb. 26, 1996

[30] Foreign Application Priority Data

Feb. 25, 1995 [EP]  European Pat. Off. ............ 95102734

[51] Int. Cl.⁶ .............. B01L 3/00; G01N 1/30; G01N 33/53
[52] U.S. Cl. ............ 422/100; 422/58; 422/81; 422/99; 422/102; 422/103; 422/104; 436/63; 356/36; 356/246
[58] Field of Search ............... 422/58, 81, 82.05, 422/99, 100, 101, 102, 103, 104; 436/63; 356/36, 246

[56] References Cited

U.S. PATENT DOCUMENTS

| | | | |
|---|---|---|---|
| 3,390,860 | 7/1968 | Kavanau | 251/9 |
| 3,639,830 | 2/1972 | Harnoncourt | 324/30 R |
| 4,043,678 | 8/1977 | Farrell et al. | 356/246 |
| 4,151,809 | 5/1979 | Johnson | 118/699 |
| 4,985,206 | 1/1991 | Bowman et al. | 422/99 |
| 5,079,959 | 1/1992 | Miyake et al. | 73/864.85 |
| 5,137,710 | 8/1992 | Smalley et al. | 424/3 |

FOREIGN PATENT DOCUMENTS

| | | |
|---|---|---|
| 0 205 108A3 | 12/1986 | European Pat. Off. . |
| 0 253 519A2 | 1/1988 | European Pat. Off. . |
| 0 310 399A3 | 4/1989 | European Pat. Off. . |
| 0 318 255A3 | 5/1989 | European Pat. Off. . |
| 0 360 487A2 | 3/1990 | European Pat. Off. . |
| 0508568 A2 | 2/1992 | European Pat. Off. . |
| 2 202 452 | 5/1974 | France . |
| 2 335 838 | 7/1977 | France . |
| 3635013A1 | 5/1988 | Germany . |
| 51-5319 | 2/1976 | Japan . |
| 1-257261 | 10/1989 | Japan . |
| 2-80937 | 3/1990 | Japan . |
| 2 231 938 | 11/1990 | United Kingdom . |
| WO92/10587 | 6/1992 | WIPO . |
| WO94/18539 | 8/1994 | WIPO . |

OTHER PUBLICATIONS

Patent Abstracts of Japan, vol. 10, No. 177 (P–470), Jun. 21, 1986 & JP–A–61–026862.

*Primary Examiner*—Harold Y. Pyon
*Attorney, Agent, or Firm*—Nikaido, Marmelstein, Murray & Oram LLP

[57] ABSTRACT

A device for processing slides-mounted samples where a slide is urged against a cell block so that a chamber is formed between cell block and slide. Via a fluid channel having a funnel at its one end, the chamber can be filled with liquid by means of a pipetting device having a connecting tip which matches the supply funnel. A device for processing samples where a contact pressure plate serves to press a slide against the cell block of the device. A device for processing samples comprising a down-pressure element which, when in non-operating mode, blocks the device from supplying liquid and where liquid can be supplied when said element is pressed down.

9 Claims, 7 Drawing Sheets

DEVICE FOR PROCESSING SLIDE-MOUNTED SAMPLES

BACKGROUND OF THE INVENTION

The invention addresses apparatus and methods for the processing of samples, in particular biological material, mounted on microscopic slides. During the processing, the samples are brought into contact with a liquid in a controlled manner.

DESCRIPTION OF THE RELATED ART

European patent application EP-A-0 508 568 to Amoco Corporation describes a system for processing slide-mounted material where the slides are placed in a cell. A contact pressure device serves to urge the slide against the cell block which is provided with a recess. The recess features both an inlet and an outlet for liquids. The recess is surrounded by a rubber seal such that a sealed chamber is defined when the slide is pressed against this seal. Complex cam-type slide-holding means are necessary to press the slide against the rubber seal. Due to the contact pressure that can be varied with the aid of this pressure device, the rubber seal can be pressed together to a smaller or greater extent in order to vary the volume formed in the chamber within given limits. A disadvantage of this device is the relative complex and hence costly design of the contact pressure device. The pressure device also requires an enormous amount of space which in turn leads to a relatively large dimensional depth of the cell which is particularly disadvantageous when several cells are to be combined to form a compact system.

International application WO 94/18539 which is also prior art describes an apparatus for staining tissue sections. The staining chambers described in this application have a cell block with a recess that is configured such that two chambers are formed when the slide is pressed against the cell block. The resulting chamber in the lower part of the cell block has the form of a gap at the lower side of which liquids can be pumped in and drawn off via a system of tubes. The upper chamber has a funnel-like shape and a slanted application surface for solid reagent preparations. In order to press the slide against the cell block, this application proposes rigidly installed leaf springs. The slide is inserted between cell block and leaf spring beginning from the top while it is necessary to overcome the counterpressure of the leaf springs. The disadvantages of this arrangement are that the leaf springs must exert relatively high pressure in order to ensure tight contact of the slide at the cell block and that this force must be overcome when the slide is inserted. Since this requires that the operator has to apply a relatively great amount of pressure onto the slide, the slide may break. In the cell, the leaf springs exert a point-focused pressure on the slide because of which it is difficult to accomplish a tight seal of the entire slide. Another disadvantage of the staining chambers described is that a complex tube system with expensive valves and pumps is necessary to fill the chambers with liquid. The relatively long tubular connections that are necessary also increase the risk of carry-overs.

European patent application EP-A-0 310 399 (Shandon Scientific Ltd.) described a chamber for staining tissues. The chamber consists of a slide and an add-on piece for the slide. At the top end of the arrangement, a funnel-like gap is located between slide and add-on part where liquid can be poured in while a capillary gap is located in the lower portion between slide and add-on part. In order to stain tissue located on the slide, liquid is placed into the funnel-like gap which then spreads in the gap due to the capillary forces. In order to displace the staining liquid from the capillary gap, another liquid is inserted into the funnel-like opening. A disadvantage of this device is that air bubbles cannot be excluded in the capillary gap so that the staining of the sample may not be uniform.

SUMMARY OF THE INVENTION

Cell with supply funnel

It was an object of the present invention to further improve the devices known to prior art for processing samples on slides such that it is possible to have a uniform staining of the samples while avoiding as far as possible expensive components such as valves and pumps and also the carry-over of liquids in the tube systems.

This object was accomplished by means of a device for processing samples on slides with liquids which comprises the following elements:

a cell with a cell block having a contact pressure surface in which a recess is provided, and a contact pressure device to urge a slide located in the cell against the contact pressure surface of the cell block in such a manner that a chamber is formed between cell block and slide because of the recess provided in the cell block, while the recess in the cell block has at least one opening at which a fluid channel ends;

a supply funnel that is linked to the fluid channel and at least one pipetting device with a connecting tip which tightly fits into the supply funnel.

Sample material and microscopic slide

Sample materials to be processed in said cell include tissue sections, smears, bacterial samples, fungi, etc. The samples are placed on slides known in prior art and fixed, if necessary. The preparation of samples on slides is commonly known in prior art; a description is therefore omitted here.

The slides commonly used in prior art are usually glass plates with a thickness of a few millimeters. It is possible to geometrically match the cells for processing the slides and the slides themselves by selecting suitable dimensions or, for example, by beveling the lower edge of the slide. It is also possible to provide the slide with a recess for inserting the samples. Plastic materials can also be employed, provided they are resistant to the liquids and the temperatures used.

Liquids for processing samples

The liquids used for processing samples are in particular dissolved stains, antibody-containing reagents, nucleic acid-containing liquids and additional liquids for processing the samples. Such additional liquids are especially solutions for maceration, freeing from fat and digesting intact cells. The antibodies or nucleic acid fragments are advantageously bound to stains or otherwise detectable labels in order to allow staining or any other labeling of the samples.

Object of the sample processing is to obtain a stain or another identification of the sample which in turn allows examination of the tissue. The staining can be of a relatively unspecific nature, for example, when rendering cell walls visible; or the staining can be specific as is the case when antibodies or nucleic acid fragments are used to indicate the presence of certain target molecules in the tissue.

With respect to sample preparation, the staining techniques and the possible stains or labels that are used, reference is made to the full contents of EP-A-O 508 568.

Cell block

The device of the invention has a cell into which a slide with the sample is placed. The cell in turn has a cell block against which the slide is pressed. The cell block is advantageously made of a thermally well-conducting material since numerous processing steps of slide-mounted samples have to be carried out at elevated temperatures. The interior of the cell block may be provided with heating elements such as electrical resistors or cooling devices such as cooling spirals. It is advantageous to provide a fluid channel, preferably a spiral or coiled channel, inside the cell block. By allowing heated liquid to pass through the fluid channel, the latter can be brought to the desired temperatures. Another, however, relatively expensive method to heat up the cell block is to bring the cell block into thermal contact with a Peltier element. Said Peltier elements can be used to heat up and cool the cell block.

If it is desired that a cell block can be removed from the cell, it is advantageous to provide contact elements, such as electrical contacts to allow a simple connection of the heating elements or the fluid channels inside the cell block to the corresponding connecting pieces of the cell. However, the heating of the cell block can also be accomplished without electrical contacts, for example, via inductive energy coupling.

The materials used for the cell block are in particular aluminum, aluminum alloys and other metals and alloys with good heat-conductive properties. Since the liquids with which the cell block is brought into contact are often aggressive, it is also suitable to employ chemically resistant special steels in addition to aluminum and aluminum alloys. In an embodiment where the heating of the cell is reduced to a minimum, it is also possible to use plastic as a material for the cell block.

The cell block has a contact pressure surface against which the slides are tightly urged. In the contact pressure surface, provision is made for a recess which defines a chamber when a slide is pressed against the contact pressure surface of the cell block. The contact pressure surface of a cell block is usually planar. The contact pressure surface is advantageously provided with a seal to provide a tight connection when the slide is pressed against the contact pressure surface. This seal is advantageously provided in the vicinity of the edge of the recess.

As described in EP-A-0 508 568, the recess can be configured within the contact pressure surface such that the resulting chamber is sealed toward the outside with the exception of in- and outlets for the fluid. The present invention advantageously proposes to configure the recess such that the chamber is accessible from the top of the cell block as is described, for example, in WO 94/18539.

The dimensions of the recess, possibly also the thickness of the seal, essentially determine the volume of a chamber. In the practice, a chamber volume between 100 and 300 $\mu$l has proven to be expedient. Since many of the liquids used for the processing of the samples are relatively expensive, e.g. antibody solutions and nucleic acid fragments, it is desired to have a relatively small chamber volume. However, the surface of the recess must be large enough to completely contain the sample material on the slide in the area of the recess. If the surface of the recess is too small, a part of the sample contacts the contact pressure surface or the seal of the cell block. This is undesired since it may lead to loss of sample material and leaks in the chamber. The depth of the recess must also be selected to be large enough, so that material that is present on the slide does not contact the back side of the recess as this may interfere with the liquid transport across the cell. Accordingly, the depth of the recess in accordance with the invention is selected such that it is at least by a few micrometers deeper than the thickness of the sample material. Suitable recess depths in accordance with the invention range between 10 $\mu$m and 500 $\mu$m.

In accordance with the invention, it is preferred to have a chamber which is tapered at its bottom, for example, by providing a bend or an inclination. Since the chamber is defined due to the interaction between recess and slide; the bend or inclination of the bottom can be achieved by selecting a suitable form for the recess. The chamber, hence, has an area where liquid arriving from said chamber is collected. It is favorable to provide in this part of the recess an opening which is linked to a fluid channel. It is then possible to almost completely remove all liquids from the cell via this fluid channel.

Contact pressure device

In order to urge the slide against the contact pressure surface of the cell block, it is possible to use a spring arrangement as described in WO 94/18539 or an arrangement as illustrated in FIGS. 2 and 13 of EP-A-0 508 568. In the present invention, it is preferred to use a plate with a vertical profile to press the slide against the contact pressure surface; said vertical profile will be described in detail hereinafter.

Fluid channel with supply funnel

An essential feature of the present invention is a fluid channel which is connected to an opening in the recess of the cell block. In a preferred manner, this opening is provided at the lowest possible point of the recess. With said fluid channel it is possible to fill the chamber of the cell block with liquid or remove liquid therefrom. Experience has shown that when the opening is provided in the lower portion of the recess, particularly at the very lowest point of the recess, it is possible to avoid the formation of air bubbles within the chamber and ensure an almost complete removal of liquid from the chamber. In the practice, a cross section of 1–2 mm for the fluid channel have proven to be favorable. It is also favorable to avoid edges throughout the entire fluid channel, even in the area of the chamber openings and bevel these areas.

In accordance with the invention, liquid is supplied to or removed from said fluid channel via a supply funnel. Funnel and fluid channel are arranged such that liquid cannot emerge from the chamber without external action. In an advantageous manner, the fluid channel is configured such that one part thereof is located above the maximum liquid level in the chamber with the funnel being provided at this part. It is thus not possible for the liquid to flow from the chamber into the funnel and cause contamination.

Pipetting device with connecting tip

The removal of liquid from the chamber and, optionally, the filling of the chamber with liquid can be accomplished with the aid of a pipetting device having a connective tip. Said tip is configured such that it tightly fits into the funnel. This system of funnel and tip renders the tube connection in the device obsolete and saves the plurality of valves and pumps.

Pipetting devices as used in the present invention are commonly known in prior art. Particularly well known are pipetting devices for clinical analyzers. A pipetting device comprises a pipetting needle and a minimum of one pump which is connected to the pipetting needle. The pipetting device also features a device for spatially moving the pipetting needle. In addition to pipetting devices as they are known for clinical analyzers, the pipetting device of invention also features a connecting tip which is attached to the pipetting needle. In accordance with the invention it is advantageous to link the pipetting needle via a spring to the device for moving it. This can be accomplished in that a spring urges the tip into the funnel to ensure a tight seal. In order to ensure a tight connection between pipetting device and funnel, the tip is formed such that it sealingly urges against the funnel. The tip can, for example, have a shape of cone, a truncated cone or a round plate. Advantageously, the tip consists at least partially of an elastic material or is coated with an elastic material. This elastic material is preferably provided at areas where the tip urges against the funnel.

Filling the cell from the top

The function of the device in accordance with the invention can be further improved by configuring the recess in the cell block such that the resulting chamber has a funnel-like enlarged opening toward it top. The resulting funnel like opening at the top of the chamber can then be used to fill liquid into the chamber from the top. In an advantageous mode of operation of the device in accordance with the invention, liquids are added into the chamber from its top while the fluid channel which is linked to the chamber is used only to remove liquid. In this manner, liquid is transported only in one single direction, so that carryover which may occur during bidirectional operation is avoided.

Additional fluid channels

Although the invention mainly addresses cells which have a fluid channel that ends into a funnel, the invention does not exclude the connection of cells via tube systems where liquids are transported with the aid of pumps. The chambers of the cells can be provided with one or several openings into which the fluid channels end. The channels are controlled via valves, and liquid is transported with the aid of one or several pumps in a net of fluid channels. For the design of such a net work of fluid channels and its control, reference is made to the complete contents of EP-A-0 508 568.

Overflow receiver

In order to increase the handling reliability, it is also advantageous to provide an overflow receiver behind the contact pressure device; said receiver receives liquid that exceeds the upper edge of the slide. The overflow receiver should also have an opening for the in- and outlet of liquid. The geometrical dimensions of the cell should be selected such that the upper edge of the slide is located below the funnel, so that liquid cannot escape from the cell via the funnel.

Reservoir

As already mentioned above, it is also possible to use antibody solutions or other sensitive biological materials as staining solutions. It is known that the solutions of the substances exhibit a relatively low stability. Experience has shown that the stability of the substances can be greatly increased if they are present in the form of a solid preparation. This is possible, for example, by embedding antibodies in a gelatin matrix or in glucose. From literature references it is known that in particular those materials which cause crystallization delays contribute to an increased stability of sensitive biological materials. It was, hence, another object of the invention to provide a device which allows the use of solid reagent preparations.

The invention proposes to provide an additional reservoir, which does not communicate with the chamber of the cell, in the vicinity of the cells. This reservoir can be used to store liquids and prepare solutions from liquids and solid preparations of biological materials. It is, for example, possible to provide a pastille in this reservoir in which the reagent is encapsulated. By adding liquid to the reservoir, a solution is freshly prepared, taken from the reservoir, and fed to the chamber. The solid preparation of this biological material can be dissolved without external influences; it is, however, advantageous to support the dissolution mechanically, e.g. by means of an agitator or by making the pipette tip vibrate. It has also proven to be advantageous for the dissolution to withdraw liquid from the reservoir several times with a pipetting device and add it back into the reservoir in order to generate a movement of the liquid which in turn accelerates the dissolution process.

Image evaluation

The invention can also propose to provide a microscope or electronic camera on the side facing away from the chamber block in order to monitor changes on the slide. It is also possible to use a transparent material, e.g. Plexiglas, to manufacture the chamber block or to provide a window within the cell block in order to monitor the sample on the slide. Said monitoring devices can be used for a final evaluation of the sample to be processed or to monitor how far the staining of the sample material has progressed. This monitoring process can be used to terminate the staining process at a suitable time.

Figure 6A:
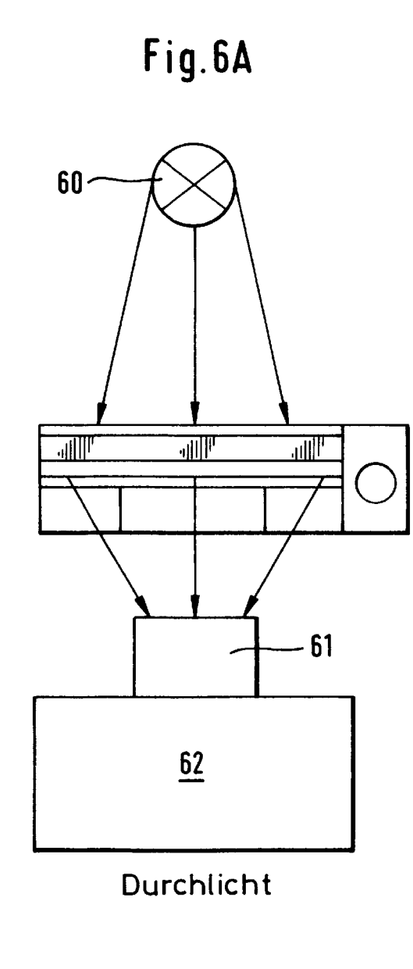
FIGS. 6A, 6B, and 6C: Arrangement for monitoring the staining in a cell
Figure 6B:
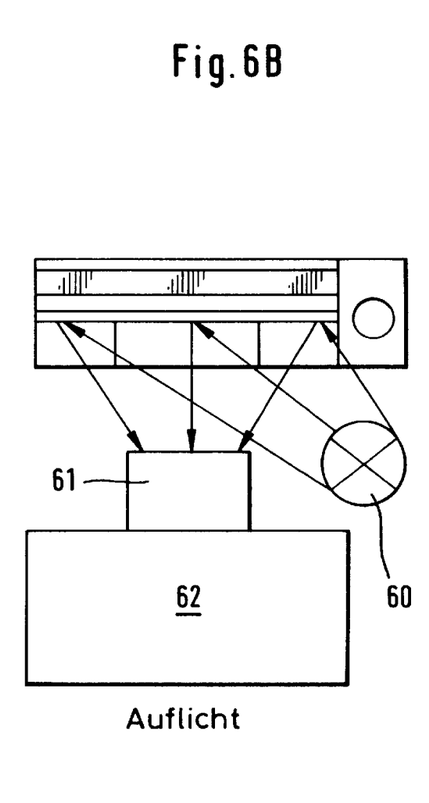
Figure 6C:
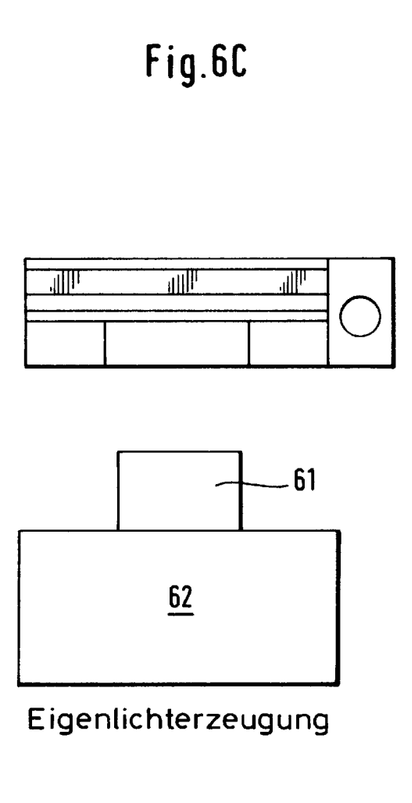

FIGS. 6A, 6B and 6C are principle sketches of possible arrangements to monitor the staining of the cell.

FIG. 6A shows an arrangement for transmitted light. Light beams that are emitted from light source (60) arrive at the rear of the cell, and pass through the contact pressure device, the slide, and the cell block. The light beams emerging from the cell block are focused by a system of lenses (61) and directed onto a detector (62). It is understood that the components of the cell through which light is transmitted have to exhibit sufficient transparency. The detector can be one that integrally evaluates the radiation (e.g. a photomultiplier or a photovoltaic element), or it is possible to select a detector that allows local resolution (e.g. CCD camera or confocal or non-confocal scanning methods).

FIG. 6B shows an arrangement where light emerging from the light source (60) is sent through the cell block and reflected by the slide or the contact pressure device. To accomplish this, the bottom of the slide or the contact pressure surface of the contact pressure device may be provided with a mirror. The reflected light is then, as already explained for FIG. 6A, processed by a system of lenses (61) and directed to a detector (62).

FIG. 6C shows an arrangement where the light is generated inside the cell, e.g. by means of chemiluminescence or electrochemiluminescence. This light passes through the cell block, is processed via a system of lenses (61) and then arrives at the detector (62).

Arrangement of cells in racks

Figure 5A:
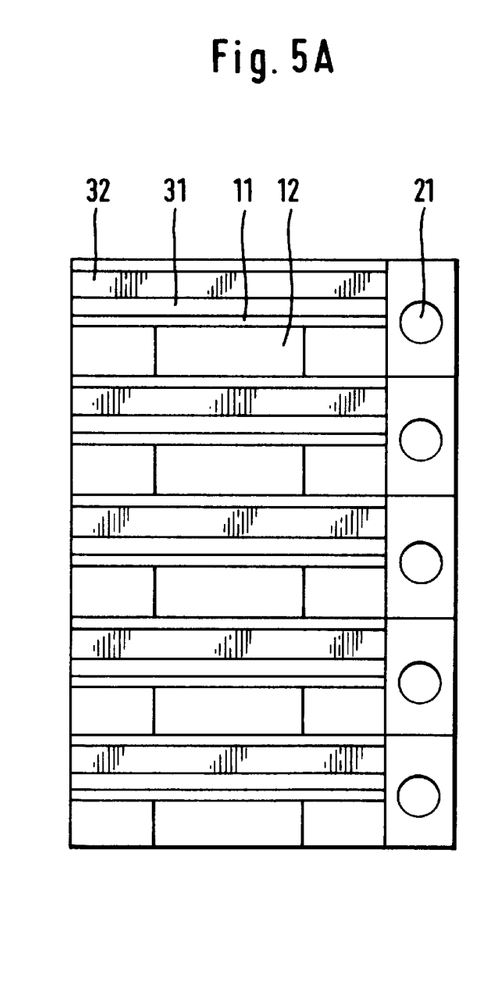
FIGS. 5A and 5B: Arrangement of cells
Figure 5B:
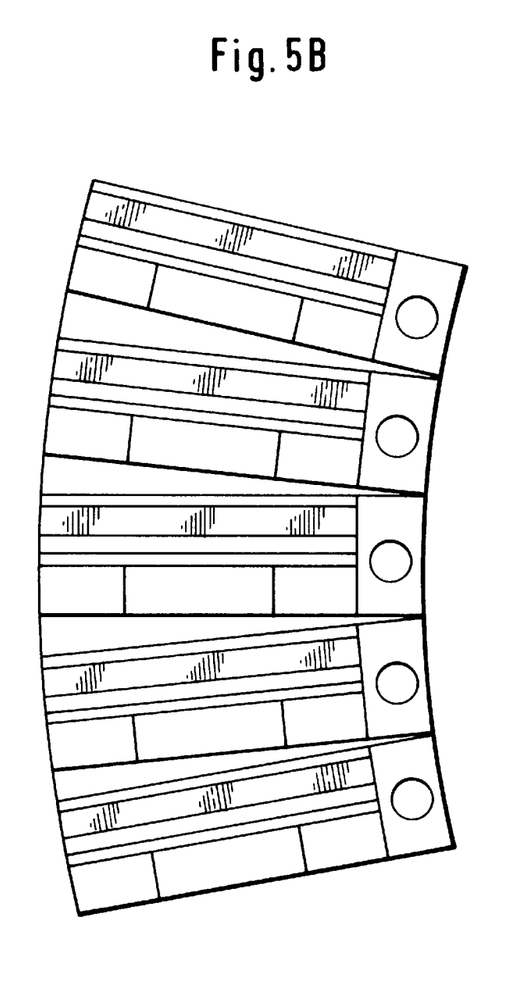

Cells in accordance with the invention are discrete units as they do not necessarily require connection to pumps and reagent containers via a system of tubes. There are, hence, less restrictions when selecting the arrangement of the cells and the means of transport as it is the case with the cells known from prior art. It is possible to combine the cells of the invention in units that are transported together. Such a procedure has already proven to be useful for sample and reagent vessels used in clinical analyzers. FIG. 5 shows two possible forms of arranging the cells.

FIG. 5A shows a linear arrangement of the cells while FIG. 5B depicts a circular arrangement. The cells are combined by linking the cells to each other in a rack.

When the cells are arranged such that free spaces are provided between individual cells, said cells can be heated up simply by immersion in a water or air bath.

Units of cells are particularly advantageous as they allow simple adaptation of the technology known from clinical analyzers to the requirements for processing samples on slides. It is possible to use the transportation devices, pipetting devices and reagent logistics as they are known from analyzers that have proven well in the practice without requiring a great deal of modifications.

BRIEF DESCRIPTION OF THE DRAWINGS

Preferred embodiments of the invention are shown in the figures.

DETAILED DESCRIPTION OF THE PREFERRED EMBODIMENTS

Embodiment for cell with supply funnel

Figure 1:
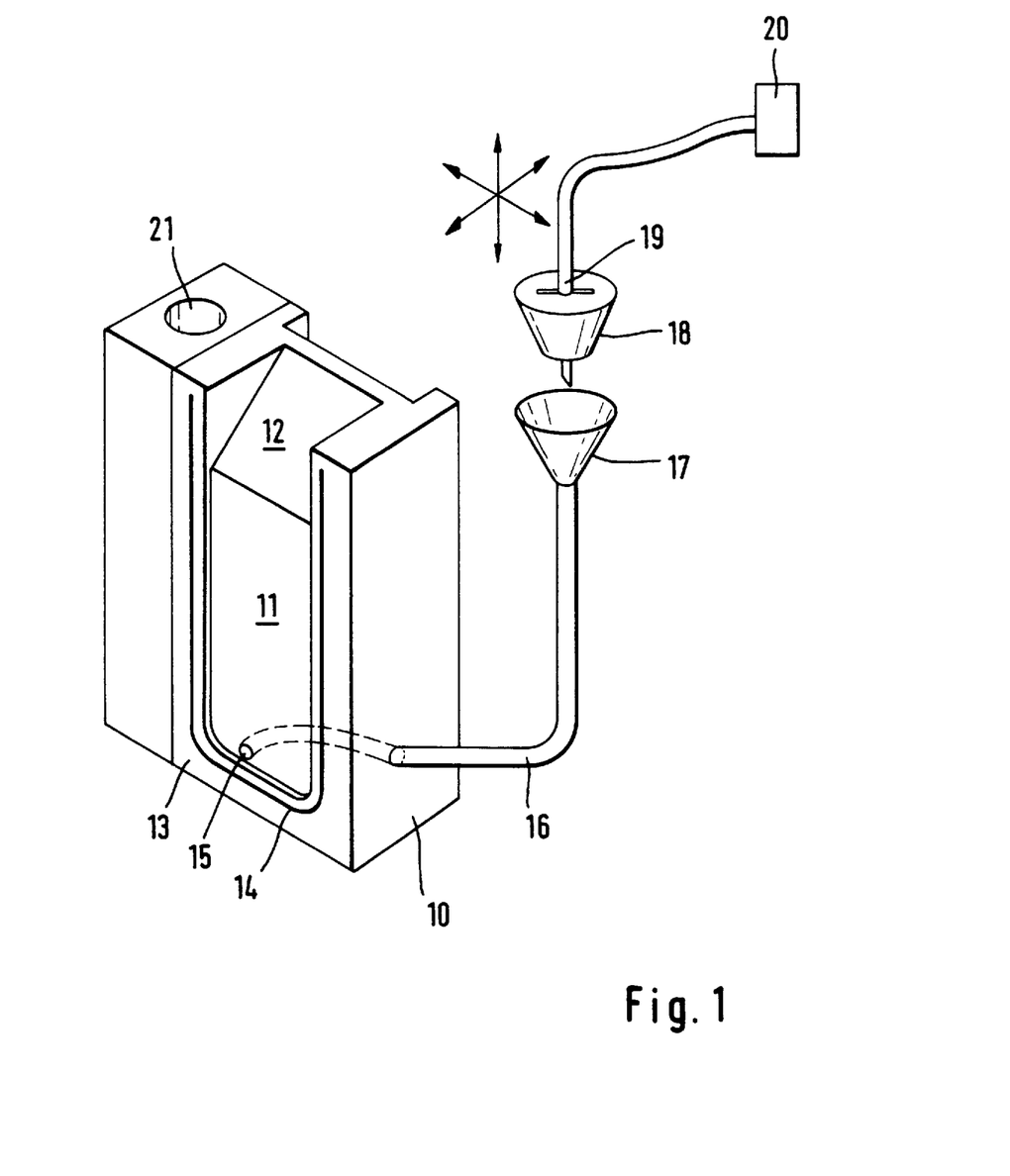
FIG. 1: Device for processing samples on slides

A device for processing samples in accordance with the invention is illustrated in FIG. 1. FIG. 1 shows a sturdy cell block (10) made of aluminum, where a recess (11) has been incorporated by means of milling. A slanted surface (12) is provided at the upper edge of recess (11). Cell block (10) has a contact pressure surface (13) which surrounds the recess (11) in a U-like shape. The surfaces of the contact pressure surface (13) and recess (11) are offset with respect to one another in a parallel manner by 0.1 to 0.3 mm. A seal (14) made of silicone rubber is provided at the contact pressure surface (13). The seal is inserted into a groove of contact pressure surface (13) or attached therein by means of gluing. In order to process samples, a slide is pressed against seal (14) so that as a consequence of the presence of recess (11) a chamber is defined between the slide and cell block (10). An opening (15) to which a fluid channel (16) is connected is provided at the bottom of the chamber. The fluid channel itself ends into the supply funnel (17). Liquid is filled into or removed from the chambers in that a connecting tip (18) is pressed into funnel (17); liquid is then added or withdrawn with the aid of pipetting needle (19). Funnel (17) can be made of numerous materials, with metal or plastic being particularly preferred. Tip (18) is preferably made of an elastic material or at least partially coated with an elastic material. Possible materials for tip (18) are rubber or silicone rubber. In order to avoid sliding of the tip (18) on the pipetting needle (19), said pipetting needle (19) has a holding device which in the present example is a cross-bar on the pipetting needle. The pipetting needle can be spatially moved with the aid of a moving device (not represented). The pipetting needle is also connected to a pump (20).

A reservoir (21) which is not connected to the chamber in the cell block is provided in the vicinity of cell block (10). This reservoir serves to receive liquids or to prepare solutions from liquids and solid reagent preparations.

Method of processing

The invention also concerns a method for processing samples on slides with liquids in a device according to claim 1, said method comprising the following steps:

the slide-mounted sample is placed into the cell;

liquid is introduced into the chamber from the top, said chamber being opened toward the top, or liquid is introduced into the chamber via a fluid channel;

liquid is removed from the chamber via the fluid channel with the aid of a pipetting device.

Usually, the slide is manually placed into the cell. It is, however, also possible to have a robot arm place the slide into the cell.

Liquid can principally be introduced in two different ways. A first option proposes to introduce liquid into the chamber from the top, said chamber also being open toward the top. In this embodiment it is advantageous if the top of the chamber is enlarged so as to facilitate the insertion of a liquid. In the second option, liquid is added into the chamber via the fluid channel (16). This is accomplished in that liquid is first drawn into a pipetting needle (19); then tip (18) is pressed into the supply funnel (17), and the liquid contained in the pipetting needle (19) is pumped into the chamber via fluid channel (16) using a pump (20). The advantage of the second option is that the formation of gas bubbles in the chamber is largely reduced.

When liquid is contained in the chamber, the sample on the slide is brought into contact with said liquid. The contact interval can either be predetermined or individually be set for each sample. Advantageously, the sample can be monitored during the time of reaction, e.g. by means of a microscope, a camera, or with the naked eye so that the total time of reaction can be selected based on the already accomplished staining or any other alteration of the sample.

When liquid is contained in the chamber, said chamber can be heated or cooled as required using the cell block. When, for example, an in situ PCR is to be carried out, the heating and cooling steps can be carried out successively.

In accordance with the invention, it is advantageous to move the liquid in the chamber during the time of reaction. This can be accomplished by changing the pressure in the chamber via the fluid channel (16) with the aid of the pipetting device.

Contact pressure plate with vertical profile

The cell shown in FIG. 1 can be operated by using contact pressure devices as described in EP-A-0 508 568 and WO 94/18539 to press the slide against the cell block. The present invention, however, also includes new contact pressure mechanism comprising a contact pressure plate with a vertical profile. Said novel contact pressure device has the advantage that it is inexpensive, has a small dimensional depth and allows inserting the slide into the cell without applying pressure.

The invention also covers a device for processing slide-mounted sample using liquids, said device comprising the following elements:

a cell with a cell block having a contact pressure surface where provision is made for a recess, and a contact pressure device to press a slide contained in the cell against a contact pressure surface of the cell block in such a manner that due to the recess in the cell block a chamber is formed between cell block and slide;

the contact pressure device features a contact pressure plate with the vertical profile on a side facing away from the cell block; and spring elements to exert pressure against the vertical profile of the contact pressure plate.

Inside the cell, the contact pressure plate is arranged essentially parallel to the contact pressure surface of the cell block. On the side facing away from the cell block, the contact pressure plate has a vertical profile so that the plates exhibit different thicknesses. On the rear of the contact pressure plate, i.e. on the side of the vertical profile, provision is made for spring elements. In given positions, said spring elements exert pressure onto the contact pressure plate so that the latter presses a slide against the contact pressure surface of the cell.

Figure 2:
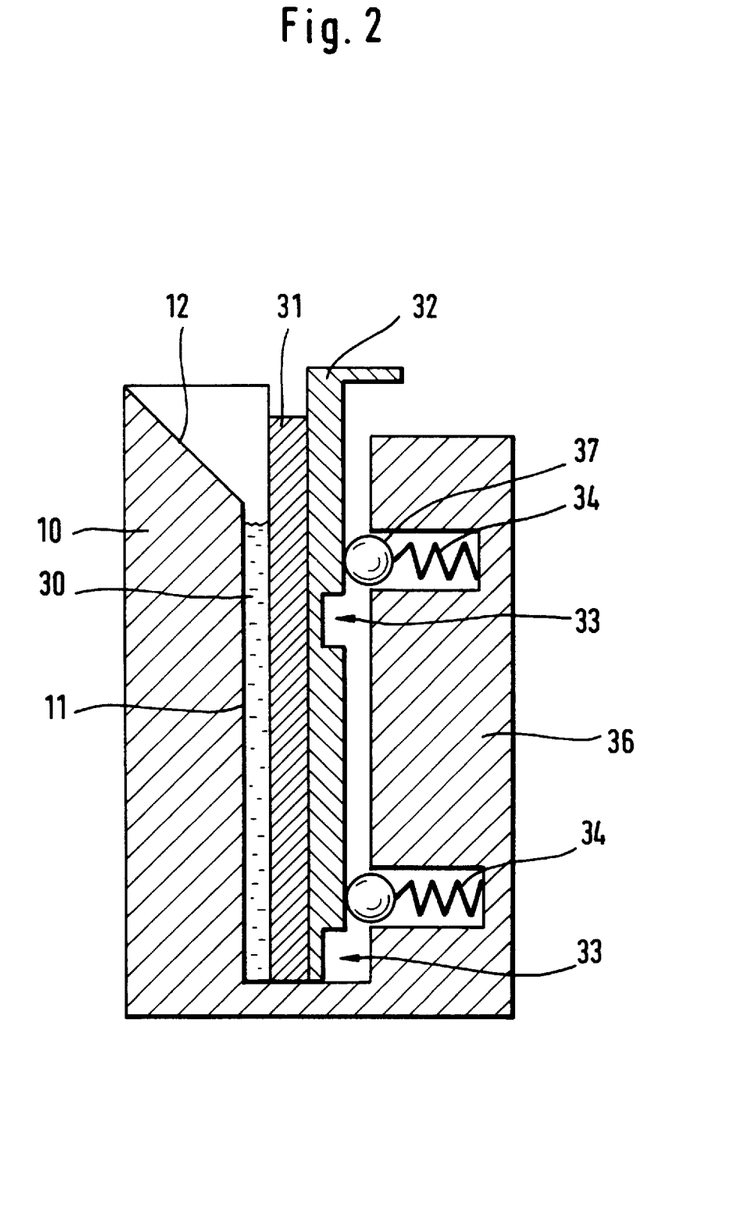
FIG. 2: Cross-sectional cell block with contact pressure device

FIG. 2 is a cross section of the cell block shown in FIG. 1 and shows a novel contact pressure device. FIG. 2 shows how liquid (30) is contained in the chamber formed between surface (11) of the recess and slide (31). On the side of slide (31) which faces away from the cell block, provision is made for a contact pressure plate (32). Spring elements (34) which are mounted to holding means (36) act on the contact pressure plate (32). In the present case, said spring elements are made of steel with a metal sphere (37) being attached to their ends. Owing to the force exerted by the steel springs, the metal sphere (37) is pressed against the contact pressure plate. In a relative position of contact pressure plate (32) to spring elements (34), as shown in FIG. 2, the contact pressure plate is pressed against the slide which in turn is pressed against the contact pressure surface (13). If the contact pressure plate (32) is moved from the position as shown toward the top, the spring elements reach the recesses (33). Owing to the small thickness of the contact pressure plate (32) in this area, the spring elements (34) are released and no longer exert pressure onto the contact pressure plate (32). This in turn causes the pressure between slide (31) and contact pressure plate (32) to be eliminated so that the slide can be readily removed from the cell.

Figure 3A:
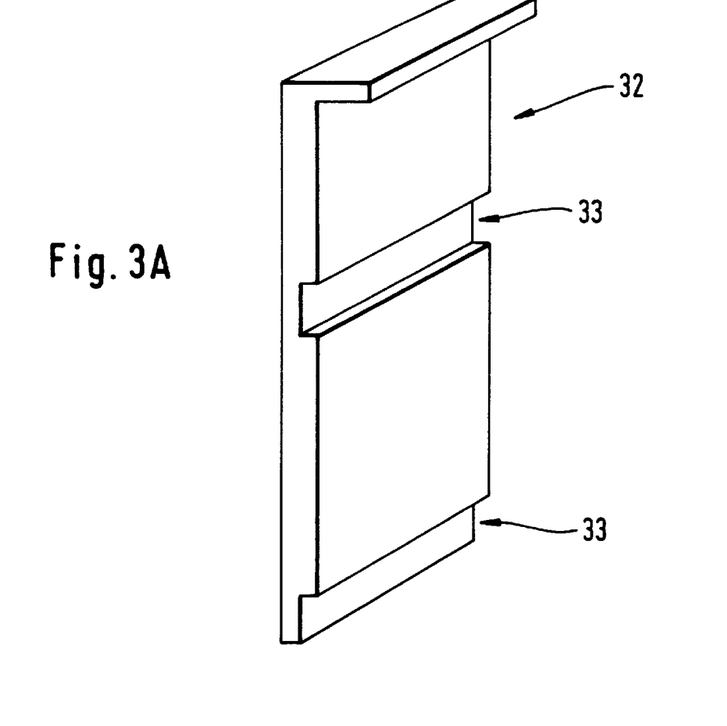
FIGS. 3A and 3B: Contact pressure plates
Figure 3B:
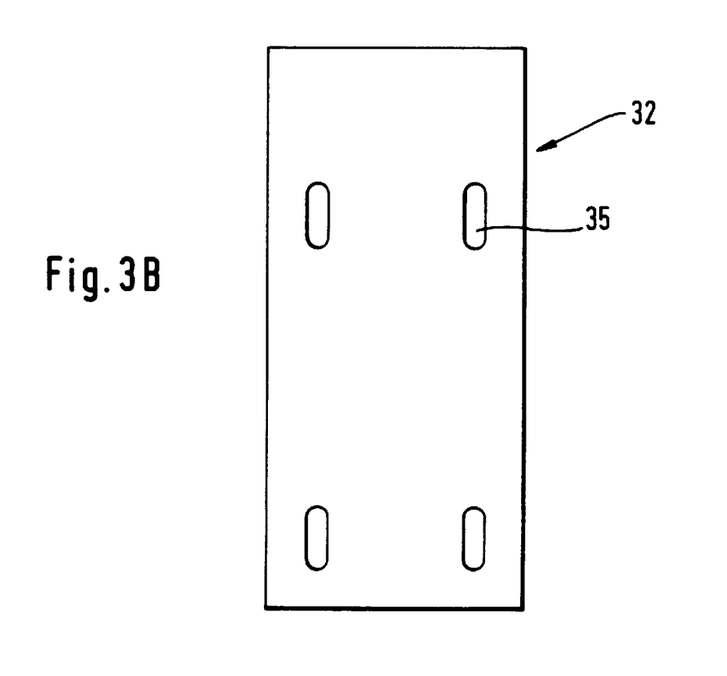

FIGS. 3A and 3B show two different embodiments of the contact pressure plate (32). Both embodiments show contact pressure plates whose vertical profiles have two different thicknesses. In the first (smaller) area of thickness, the distance between contact pressure plate of the cell block and contact pressure plate is large enough that a slide between contact pressure plate and contact pressure surface is not pressed against said contact pressure surface. In a second area of thickness of the contact pressure plate, the distance is such that the contact pressure plate presses a slide located between cell plate and the contact pressure surface against said surface owing to the force exerted by the spring elements. The contact pressure plate shown in FIG. 3A corresponds the one of FIG. 2. From FIG. 3A it can be understood how the recesses (33) are arranged on the rear of the contact pressure plate (32).

FIG. 3B shows the contact pressure plate that is relatively similar to the one of FIG. 3A. The contact pressure plate (32) shown in FIG. 3B has four recesses (35) on its rear side. The recesses (35) assume essentially the same function as the recesses (33). When the spring elements (34) are located above or underneath the recesses (35), the active thickness of the contact pressure plate (32) is relatively large and said contact pressure plate (32) acts as a holding means for the slide. If, however, the contact pressure plate (32) is in a position where the spring elements (34) engage the recesses (35), said elements are released and there is no pressure applied onto the slide. The embodiment of the contact pressure plate (32) according to FIG. 3B has the advantage that the plate is held laterally if the spring elements are engaged in the recesses (35). Moreover, this embodiment also has the advantage that a certain resistance must be overcome when the plate is removed from the cell.

The embodiments shown in FIGS. 3A and 3B show possible examples of contact pressure plates. The invention proposes to provide a vertical profile with areas of different thickness at the rear of the contact pressure plate (32). In the most simple case of a holding plate in accordance with the invention, the rear of said plate is planar and has no recesses or different thicknesses. In such a simple configuration of a holding plate, there are no positions where no pressure is exerted onto the slide if the plate is inserted into the cell. When such a holding plate is employed, the slide is first placed into the cell and the holding plate is then inserted behind the slide. As opposed to the leaf springs of WO 94/18539 this simple embodiment of a holding plate already has the advantage that the slides can be incorporated in the cell without applying pressure, thus reducing the risk of damaging glass. Moreover, it is an advantage of the holding plate that due to the rigid plate, the focused forces of the spring elements are distributed across the slide, leading to a more uniform pressure being applied onto the slide. The expert may also vary the configuration of the spring elements. It is, for example, possible to replace the illustrated spiral springs by gas pressure springs or the like. Even the use of leaf springs as described in WHO 94/18539 is possible with the holding plates in accordance with the invention. However, while WHO 94/18539 describes springs which apply pressure to the center of the slides, the invention preferably proposes to arrange a spring element such that pressure is applied to the holding plate at two or even four areas. In FIG. 2 it can be understood that the spring elements are preferably arranged in the lower or upper area of the slide. Moreover, it is also advantageous to apply pressure to the holding plate on four sides which are located at the four corners of the slide.

It is also possible to replace the metal spheres provided at the end of the springs with plastic packs.

In addition to the inexpensive implementation of the holding device in accordance with the invention and its small dimensional depth, it is another advantage of this device that the holding plate can be configured such that it can be removed from the cell. Thus, it is possible to clean the contact pressure plate or replace it readily.

Yet another advantage of the contact pressure plate is that it allows uniform transmission of the forces onto the slide. The focused action of the force that is applied onto the contact pressure plate is distributed across the slide (31) because of the form stability of the contact pressure plate. Owing to this more uniform distribution, the slide is subject to less mechanical stress, thus avoiding leaks between slide and seal.

Particularly suitable materials for the contact pressure plates are especially plastics, which can be processed via injection molding. However, it is principally also possible to use metals that exhibit sufficient resistance against the liquids used. Preferred materials are those exhibiting a relatively high rigidity so that the pressure which is applied onto the contact pressure plate by the spring elements is exerted in a uniform manner.

In cases where the sample is monitored from the rear of the slide, it is possible to use transparent materials for the contact pressure plate. Particularly suitable are plastics such as polymethylmethacrylate and polystyrene.

To facilitate handling, the contact pressure plate may in its upper area be provided with a corrugated handle. As shown in FIGS. 2 and 3A, said handle can also be tilted with respect to the holding plate in order to further facilitate handling.

Method of processing using the contact pressure plate

A method for processing slide-mounted samples using the novel contact pressure device preferably comprises the following steps:
  inserting a slide into the cell,
  vertical movement of the contact pressure plate to assume
    a position where said contact pressure plate presses the
    slide against a contact pressure surface,
  filling the chamber with liquid,
  removing liquid from the chamber,
  removing the slide from the cell.

When a removable contact pressure plate is used, the above described method can be preceded by a step where the contact pressure plate is inserted into the cell.

The methods for processing begin in that the contact pressure plate is located in a position where the distance between contact pressure plate and contact pressure surface of the cell is large enough that a slide can be inserted into the cell without applying a substantial amount of force. Subsequently, the contact pressure plate is moved downwardly, while the recesses at the contact pressure plate are also moved so that the spring elements are pressed against the contact pressure plate. Once the slide has been brought into this position, the actual processing of the sample takes place in that liquid is inserted into the chambers while cooling or heating chambers, if necessary. Before the slide is removed from the cell, the liquid is withdrawn from the chamber. The so-processed slide is removed in that the contact pressure plate is moved vertically. Usually, the contact pressure plate is removed by pulling it upwardly, so that the recesses on the contact pressure plate reach the level of the spring element and the pressure exerted by the contact pressure plate onto the slide is released. The slide can now be removed from the cell without requiring a major amount of force.

Down-pressure element

The problem involved with devices as known in prior art which propose to fill the staining chambers via a system of pumps is that relatively expensive valves are necessary to couple the individual cells to the fluid system or block them therefrom. The necessity of expensive electrically controllable valves could be eliminated by one aspect of the present invention which addresses a low-pressure element.

Advantageously, it is possible to use the movement of the slide when it is inserted into the cell or the movement of the contact pressure plate of the invention to operate a mechanical valve. The operator of the device is therefore not required to undertake any additional actions.

The low-pressure element ensures that cells, which are not used for processing samples, are separated from the liquid circulation. This is particularly advantageous when a system is used which consists of several processing devices. This arrangement prevents expensive reagent solutions from being consumed for chambers with no slide.

The invention, hence, addresses a device for processing sample on slides with liquids which comprises the following elements:

a cell with a cell block having a planar contact pressure surface in which provision is made for recess and a contact pressure device to press a slide contained in the cell against the contact pressure surface of the cell block in such a manner that due to the recess provided in the cell block, a chamber is formed between cell block and slide; that chamber having an opening to which a fluid channel is connected which in turn is connected to at least one reservoir and one pumping device, a down-pressure element which blocks the fluid channel with respect to the at least one reservoir or pumping device when said element is in its non-operating mode, and opens the fluid channel when it is pressed down.

Figure 4A:
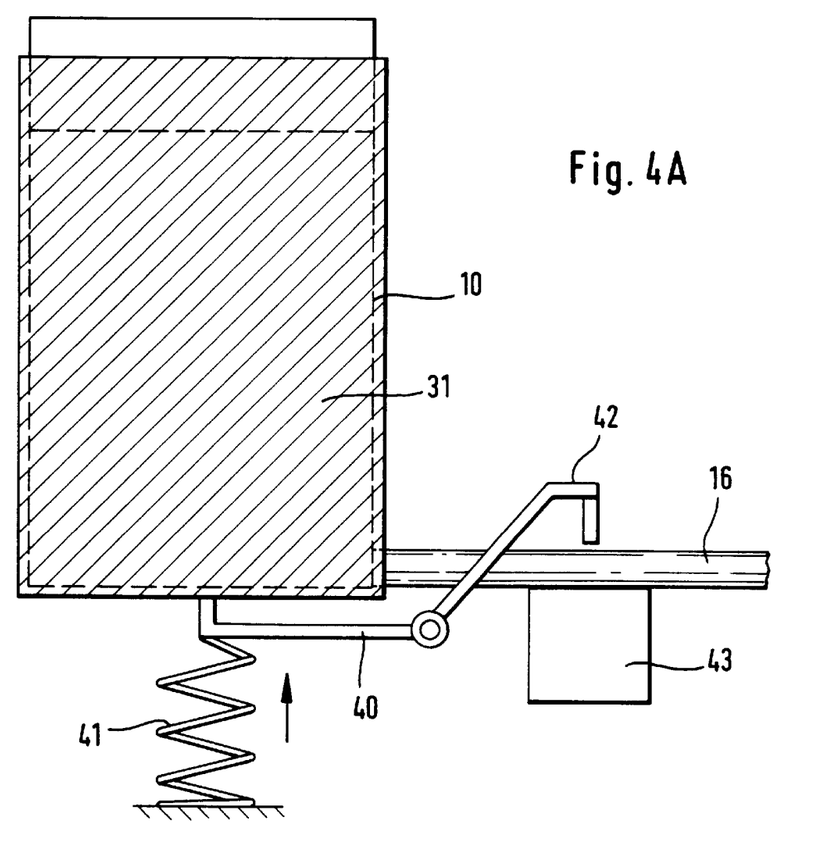
FIGS. 4A and 4B: Device with low-pressure elements
Figure 4B:
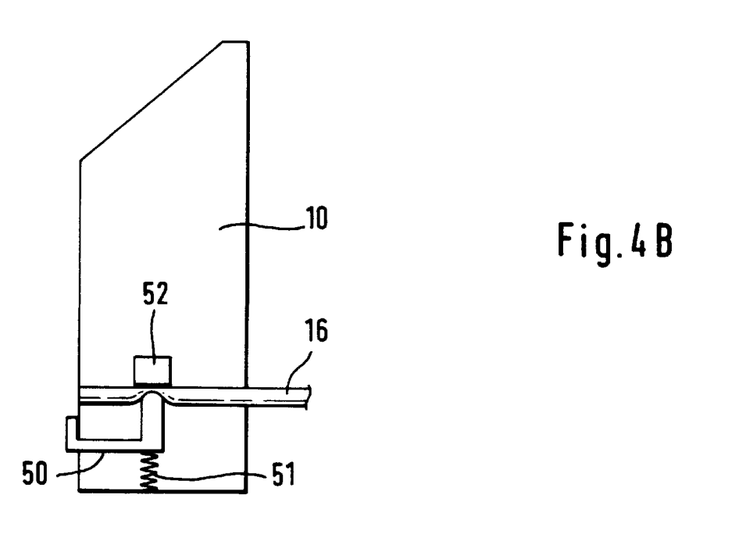

FIGS. 4A and 4B show examples of two embodiments where the fluid connection of the cell and the tube system is controlled via the down-pressure elements of the invention. FIG. 4A shows a first embodiment where a lever (40) is pressed down by the slide (31) as soon as the slide is placed into the cell. The lower edge of slide (31) presses onto lever (40) and overcomes the tension of the spring (41). A second lever (42) that is rigidly connected to the first lever (40) is then pushed upwardly, thus opening the fluid channel (16). If slide (31) is removed from the cell, spring (41) pushes the lever (40) upwardly and lever (42) executes a downward movement. Fluid channel (16) which consists of a compressible material at least in the part below lever (42) is compressed between lever (42) and mounting block (43).

FIG. 4B shows a second embodiment with a lever (50) which is pushed upwardly via spring (51) and presses the fluid channel (16) against mounting block (52) resulting in a compression of said channel (16). When the slide is inserted into the cells, its lower edge presses against lever (50), thus moving the entire lever downwardly and opening the fluid channel (16).

For compression of the fluid channel, said channel must be made of a compressible material at least in the area between the lever and the respective mounting block. Suitable fluid channels can be made, for example, of polyethylene or silicone rubber.

When configuring the springs (41, 51), it must be taken into account that said springs have to completely compress fluid channel (16), on the one hand, and, on the other hand, breaking of glass should be avoided when the slide is pressed down.

Device with reservoirs on a slanted surface

Figure 7A:
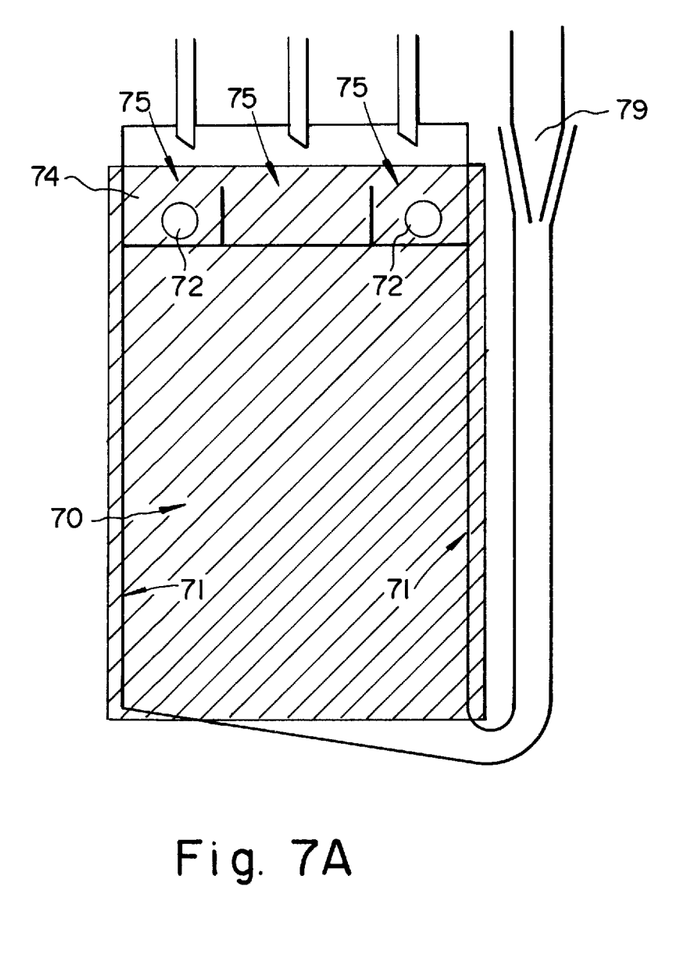
FIGS. 7A and 7B: Device with reservoir on slanted surface.
Figure 7B:
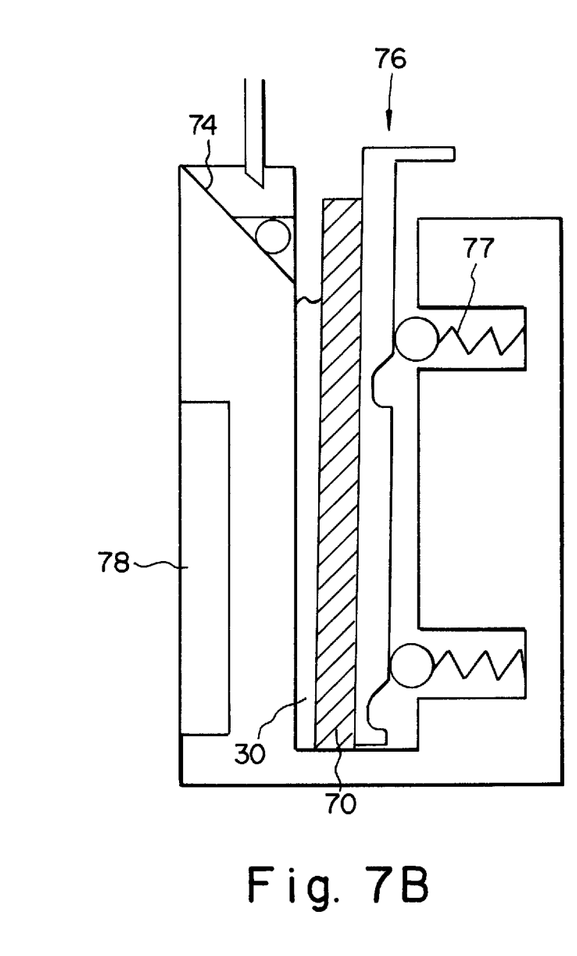

FIG. 7 shows another embodiment of the device in accordance with the invention. From the top view of the chamber in FIG. 7A across the slide (70) (hatched lines), it can be seen that the bottom of the chamber is slanted and that the funnel is provided at its lowest point; the function of said funnel has already been described in connection with FIG. 1. Liquid can be added and removed from the funnel with the aid of a pipette (79). A contract pressure plate (76) serves to press the slide against the edges (71). FIG. 7B shows a modified embodiment of the contact pressure plate with two recesses; these recesses are provided a continuous transition to the surface of the contact pressure plate as it is the case with the contact pressure plate in FIG. 2. The spring elements (77) correspond to those of FIG. 2. A difference of the device of FIG. 7 with respect to the embodiments of FIGS. 1 and 2 lies in the configuration of the reservoir for the reagents. FIG. 7 shows that on the inclination (74) of the chamber, provision is made for two smaller chambers which form two reservoir (73). These reservoirs may contain, for example, solid reagent such as pellets (72) that are then dissolved in a liquid. When the cross bars are located low enough that the maximum fluid level in the reservoir (73) is below the chamber opening, liquid that flows over the edge of the reservoir is then collected in the chamber. It is thus possible to rinse the reservoirs by adding liquids and transport reagent into the chamber. Alternatively to rinsing the reservoir, it is also possible to add the reagent from the reservoir into the chamber with the aid of pipetting needle. In the middle of the inclination, there is no reservoir so that this area can be used as a pipetting channel (75) for the direct addition of the liquid into the chamber.

We claim:

1. A device for processing slide-mounted samples, said device comprising:

at least one cell block having a slide accommodation area for receiving a slide therein, said at least one cell block having a contact pressure plate surface thereupon, with a recess in said contact pressure plate surface, said cell block being configured to have the slide disposed adjacent said contact pressure plate surface;

contact pressure means for biasing the slide against the contact pressure plate surface of the at least one cell block, wherein a chamber is formed between a surface of the slide and an inner surface of the recess, said contact pressure means comprising a pressure plate having a vertical surface on a first side thereof, with a second side thereof configured to engage the slide; said device further comprising biasing means for biasing the contact pressure means against the slide, said biasing means configured to engage the first side of the pressure plate, wherein said pressure plate comprises a first portion having a first thickness, and a second portion having a second thickness, and wherein the biasing means are configured to selectively engage one of the first thickness and the second thickness, said first thickness being greater than said second thickness, wherein when said biasing means engage the first thickness, the pressure plate biases the slide against the contact pressure plate surface of the cell block, and wherein when said biasing means engage the second thickness of the pressure plate, no biasing force is applied to the slide from the pressure plate.

2. A device according to claim 1, wherein the pressure plate is removable from the cell block.

3. A device according to claim 1, wherein said biasing means comprises spring elements.

4. A device according to claim 1, wherein the second thickness of the pressure plate is defined by at least one recess in the first side thereof.

5. A device for processing slide-mounted samples, said device comprising:

at least one cell block having a slide accommodation area for receiving a slide therein, said at least one cell block having a contact pressure plate surface thereupon, with a recess in said contact pressure plate surface, said cell block being configured to accommodate the slide adjacent said contact pressure plate surface;

contact pressure means for biasing the slide against the contact pressure plate surface of the at least one cell block, wherein a chamber is formed between a surface of the slide and an inner surface of the recess, said chamber having at least one opening therein;

fluid channel means for supplying fluid to said chamber, said fluid channel means connected to at least one opening and to a liquid source; and shutoff means coupled to the fluid channel means for opening and closing the fluid channel means, wherein the shutoff means is disposed at a bottom of the slide accommodation area, and wherein an insertion of the slide into the slide accommodation area activates the shutoff means to open the fluid channel means.

6. A device as recited in claim 5, wherein said fluid channel means includes an elastic portion thereof, said elastic portion being compressible by the shutoff means.

7. A device as recited in claim 5, wherein the shutoff means comprises a rotatable pressure element which rotates on an axis such that a downward force exerted by the slide onto the pressure element rotates the shutoff means to open the fluid channel means.

8. A device as recited in claim 5, wherein said shutoff means comprises a pressure element which, in a non-operating mode, closes the fluid channel means, and opens the fluid channel means in a operating mode when downward pressure is applied thereto.

9. A device as recited in claim 8, wherein the shutoff means comprises a spring means for biasing the shutoff means against the elastic portion of the fluid channel means, thereby closing the fluid channel means.

* * * * *